United States Patent
Haibach

(10) Patent No.: US 11,554,236 B2
(45) Date of Patent: Jan. 17, 2023

(54) PATIENT INTERFACE DEVICE HAVING MAGNETIC COUPLING FEATURES

(71) Applicant: KONINKLIJKE PHILIPS N.V., Eindhoven (NL)

(72) Inventor: Richard Thomas Haibach, Verona, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 422 days.

(21) Appl. No.: 16/712,249

(22) Filed: Dec. 12, 2019

(65) Prior Publication Data
US 2020/0197649 A1   Jun. 25, 2020

Related U.S. Application Data

(60) Provisional application No. 62/784,572, filed on Dec. 24, 2018.

(51) Int. Cl.
*A61M 16/08* (2006.01)

(52) U.S. Cl.
CPC . *A61M 16/0816* (2013.01); *A61M 2205/0272* (2013.01)

(58) Field of Classification Search
CPC ...................... A61M 16/0816; A61M 2205/02
USPC ..................................................... 128/202.27
See application file for complete search history.

(56) References Cited

U.S. PATENT DOCUMENTS

| 8,042,542 | B2 | 10/2011 | Dantanarayana et al. |
| 9,308,345 | B2 | 4/2016 | Chalvignac |
| 9,480,809 | B2* | 11/2016 | Guney ................ A61M 16/06 |
| 9,737,678 | B2* | 8/2017 | Formica ........... A61M 16/0057 |
| 9,802,018 | B2 | 10/2017 | Ging et al. |
| 10,080,856 | B2* | 9/2018 | McLaren ............ A61M 16/06 |
| 10,130,785 | B2* | 11/2018 | Dravitzki ........ A61M 16/0616 |
| 10,206,571 | B2* | 2/2019 | Ewers .............. A61M 16/0069 |
| 10,265,494 | B2* | 4/2019 | Cortez, Jr. ....... A61M 16/0808 |
| 11,278,692 | B2 | 3/2022 | Amarasinghe |

(Continued)

FOREIGN PATENT DOCUMENTS

EP         2679266 A1        1/2014

OTHER PUBLICATIONS

International search report for PCT/EP2019/086197 dated Dec. 19, 2019.

*Primary Examiner* — Craig M Schneider
*Assistant Examiner* — David R Deal
(74) *Attorney, Agent, or Firm* — Michael W. Haas

(57) ABSTRACT

A patient interface device includes a frame having a central portion with a patient facing side, an opposite outward facing side, a first plurality of magnetic elements secured on or in the patient facing side, and a first aperture defined therethrough. The first aperture having a first portion extending from the outward facing side toward the patient facing side which is structured to be coupled to a delivery conduit and a patient side portion defined by a wall which extends outward from the patient facing side forming a hub. The device further includes a cushion having a patient contacting side which is structured to sealingly engage about an orifice or orifices of a patient, an opposite frame contacting side including a second aperture defined therein which is sized and configured to engage about the hub, and a second plurality of magnetic elements for magnetically coupling the cushion to the frame.

20 Claims, 9 Drawing Sheets

(56) References Cited

U.S. PATENT DOCUMENTS

| | | | |
|---|---|---|---|
| 2005/0155604 A1* | 7/2005 | Ging | A61M 16/0616 |
| | | | 128/207.11 |
| 2014/0338664 A1* | 11/2014 | Ging | A61M 16/0683 |
| | | | 128/202.27 |
| 2015/0250972 A1 | 9/2015 | Haibach et al. | |
| 2015/0335846 A1 | 11/2015 | Romagnoli | |
| 2016/0082214 A1 | 3/2016 | Barlow et al. | |
| 2017/0333660 A1* | 11/2017 | Haibach | A61M 16/0683 |
| 2018/0140796 A1* | 5/2018 | Haibach | A61M 11/00 |
| 2019/0125998 A1* | 5/2019 | Baiko | A61M 16/0666 |
| 2019/0175863 A1 | 6/2019 | Hocking et al. | |
| 2020/0197649 A1* | 6/2020 | Haibach | A61M 16/0683 |

\* cited by examiner

ABSTRACT# PATIENT INTERFACE DEVICE HAVING MAGNETIC COUPLING FEATURES

CROSS-REFERENCE TO RELATED APPLICATIONS

This patent application claims the priority benefit under 35 U.S.C. § 119(e) of U.S. Provisional Application No. 62/784,572, filed on Dec. 24, 2018, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient and, more particularly, patient interface devices having magnetic coupling features for use in coupling a cushion and frame thereof.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve a gas flow generator to produce a flow of breathing gas, and the placement of a patient interface device including a mask component on the face of a patient. The gas flow generator produces positive air pressure by taking air in from the surroundings and spinning a fan to push the air out of the machine, through a delivery conduit, and into the patient interface device to be delivered to the patient.

Traditional cushion members for patient interface devices include a sealing portion that is structured to engage the face of a patient in order to provide a seal therewith and a frame which is typically formed from a more rigid material which is generally used to hold the cushion in a desired position and provide attachment points for a headgear member used to secure the frame and cushion to the head of a patient. Typically, the cushion and frame are coupled in a manner so as to be readily uncoupled to allow for cleaning and/or replacement of one of the members. Accordingly, such coupling generally needs to be strong enough so as to not unexpectedly come undone, while also not being still being able to be disassembled and reassembled in a fast and generally simple fashion.

SUMMARY OF THE INVENTION

Embodiments of the present invention provide coupling arrangements which improve upon conventional designs. As one aspect of the invention, a patient interface device for use in delivering a flow of breathing gas to the airway of a patient comprises: a frame having a central portion formed as a generally thin member, the central portion comprising: a patient facing side; an opposite outward facing side; a first aperture defined therethrough, the first aperture having a first portion extending from the outward facing side toward the patient facing side which is structured to be coupled to a delivery conduit providing the flow of breathing gas, and a patient side portion defined by a wall which extends outward from the patient facing side forming a hub; and a first plurality of magnetic elements, each magnetic element of the first plurality of magnetic elements being secured on or in the patient facing side; and a cushion comprising: a patient contacting side which is structured to sealingly engage about an orifice or orifices of a patient; a frame contacting side disposed opposite the patient contacting side, the frame contacting side including a second aperture defined therein which is sized and configured to engage about the hub of the central portion of the frame and is structured to provide for passage of the flow of breathing gas passing through the first aperture of the central portion of the frame to enter a cavity defined in the cushion generally between the patient contacting side and the frame contacting side; and a second plurality of magnetic elements, each magnetic element of the second plurality of magnetic elements being secured on or in the frame contacting side of the cushion in a corresponding position to each magnetic element of the first plurality of magnetic elements of the frame such that the cushion is magnetically coupled to the frame.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
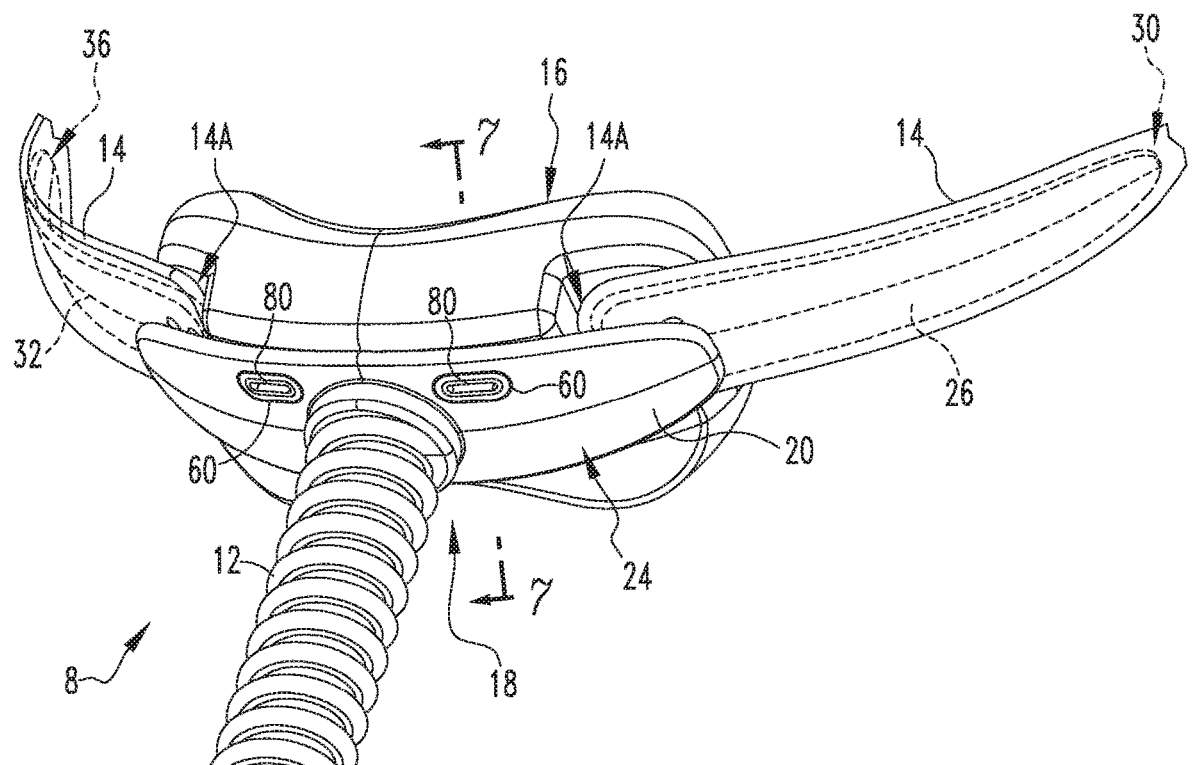
FIG. 1 is a front isometric view of a patient interface device and a portion of a conduit shown connected to a gas flow/pressure generating device (shown schematically) to form a system adapted to provide a regiment of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other (i.e., touching). As used herein, "fixedly coupled" or "fixed" means that two components are coupled so as to move as one while maintaining a constant orientation relative to each other.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, left, right, upper, lower, front, back, on top of, and derivatives thereof, relate to the orientation of the elements shown in the drawings and are not limiting upon the claims unless expressly recited therein. As employed herein, the term "and/or" shall mean one or both of the elements separated by such term. For example, "A and/or B" would mean any of: i) A, ii) B, or iii) A and B.

A system 2 adapted to provide a regimen of respiratory therapy to a patient according to one exemplary embodiment of the invention is generally shown in FIG. 1. System 2 includes a pressure generating device 4 (shown schematically), a delivery conduit 6 (shown schematically), a patient interface device 8 having a fluid coupling conduit 10 coupled via a conduit segment 12, and a headgear (only straps 14 thereof are shown). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10 and conduit segment 12. In the exemplary embodiment illustrated in FIG. 1, fluid coupling conduit 10 is straight connector, however, it is to be appreciated that other suitable couplings may be employed without varying from the scope of the present invention. It is also to be appreciated that conduit segment 12 may be eliminated, and thus delivery conduit 6 connected directly to patient interface device 8 or connected via an aforementioned coupling without varying from the scope of the present invention. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, flow/pressure generating device 4 is also referred to as a gas flow generating device, because flow results when a pressure gradient is generated. The present invention contemplates that flow/pressure generating device 4 is any conventional system for delivering a flow of gas to an airway of a patient or for elevating a pressure of gas at an airway of the patient, including the pressure support systems summarized above and non-invasive ventilation systems.

Continuing to refer to FIG. 1, as well as FIG. 2, patient interface device 8 includes a cushion 16 coupled to a frame 18 via a magnetic arrangement, discussed in detail below. Cushion 16 may be formed of any pliable material (e.g., without limitation, silicone). Frame 18 may be formed of a substantially rigid material (e.g., without limitation, one or more plastics).

Figure 2:
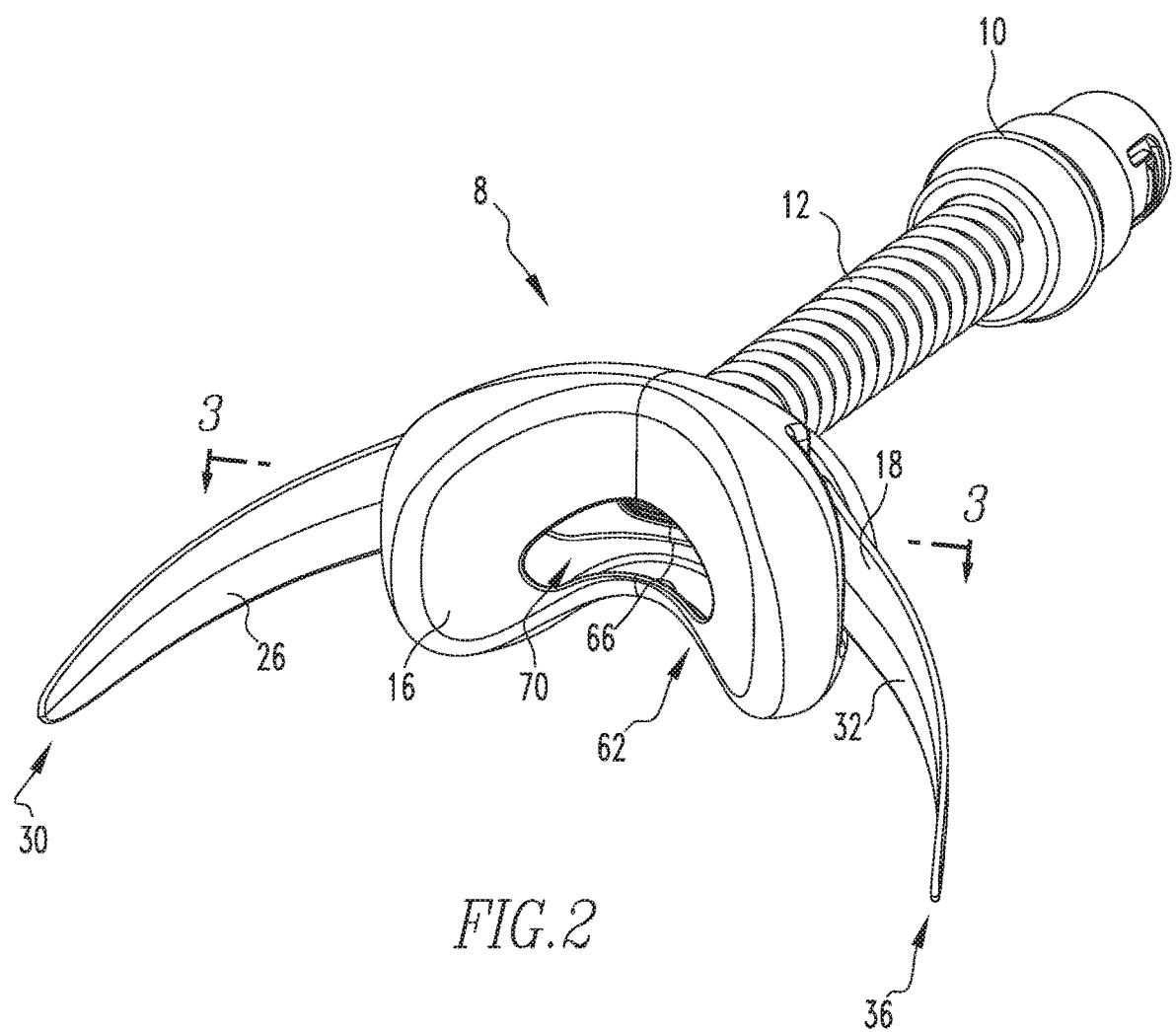
FIG. 2 is a rear isometric view of the assembled frame and cushion of the patient interface device of FIG. 1.
Figure 3:
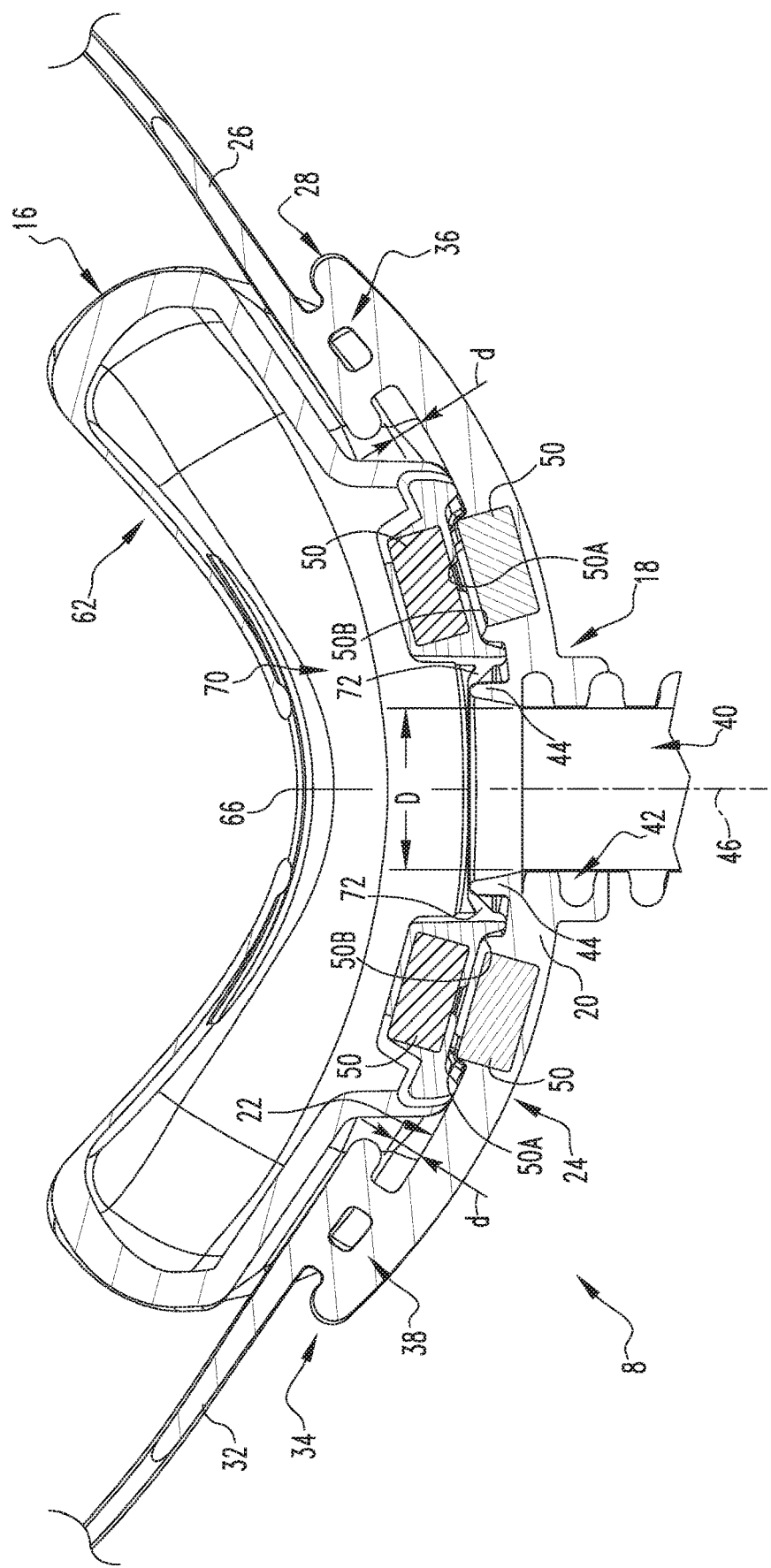
FIG. 3 is a sectional isometric view of the assembled frame and cushion of FIG. 2 taken along line 3-3 of FIG. 2.
Figure 4:
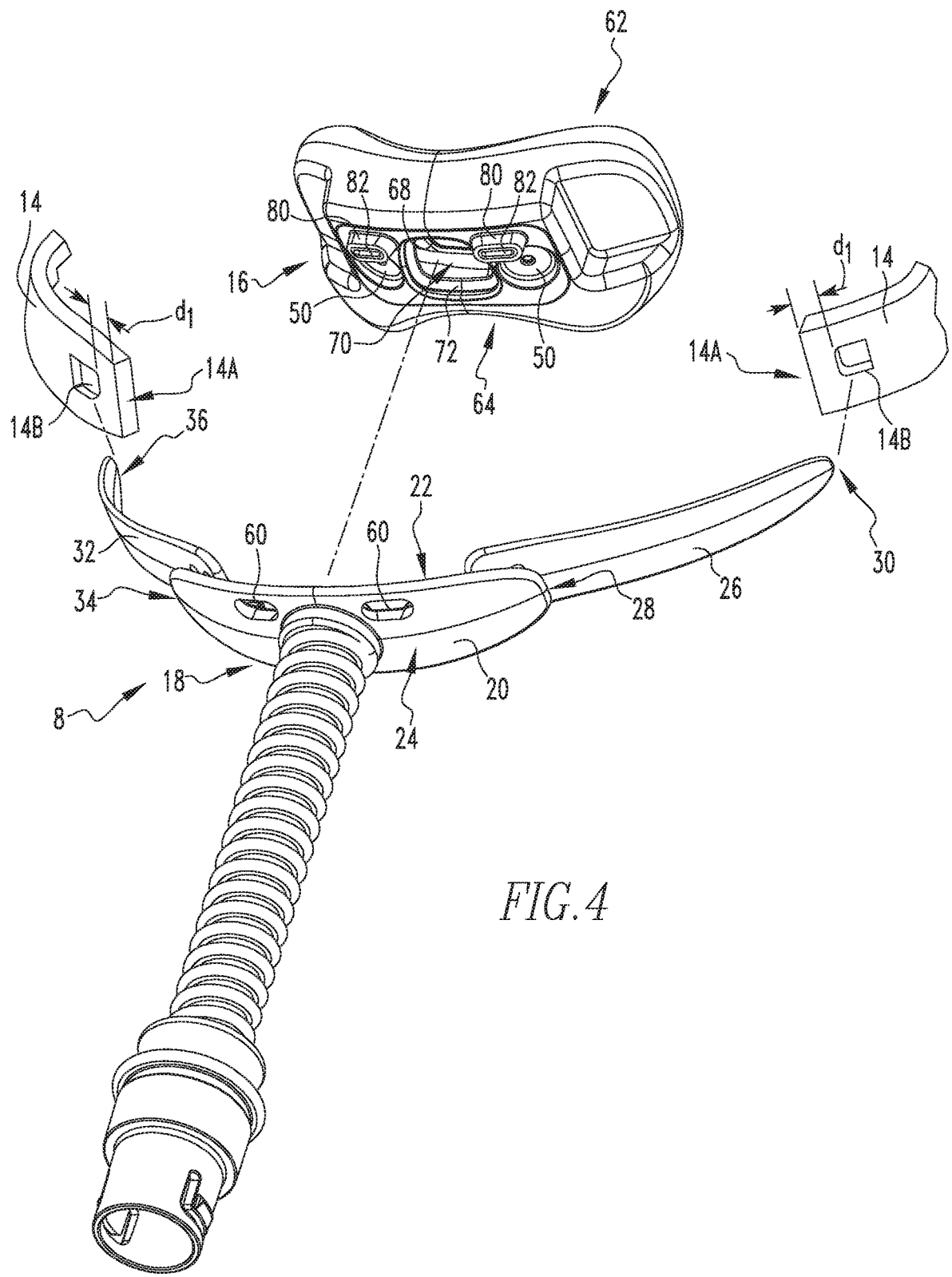
FIG. 4 is an exploded front isometric view of the patient interface device of FIG. 1 shown with the cushion and headgear thereof exploded from the frame.
Figure 5:
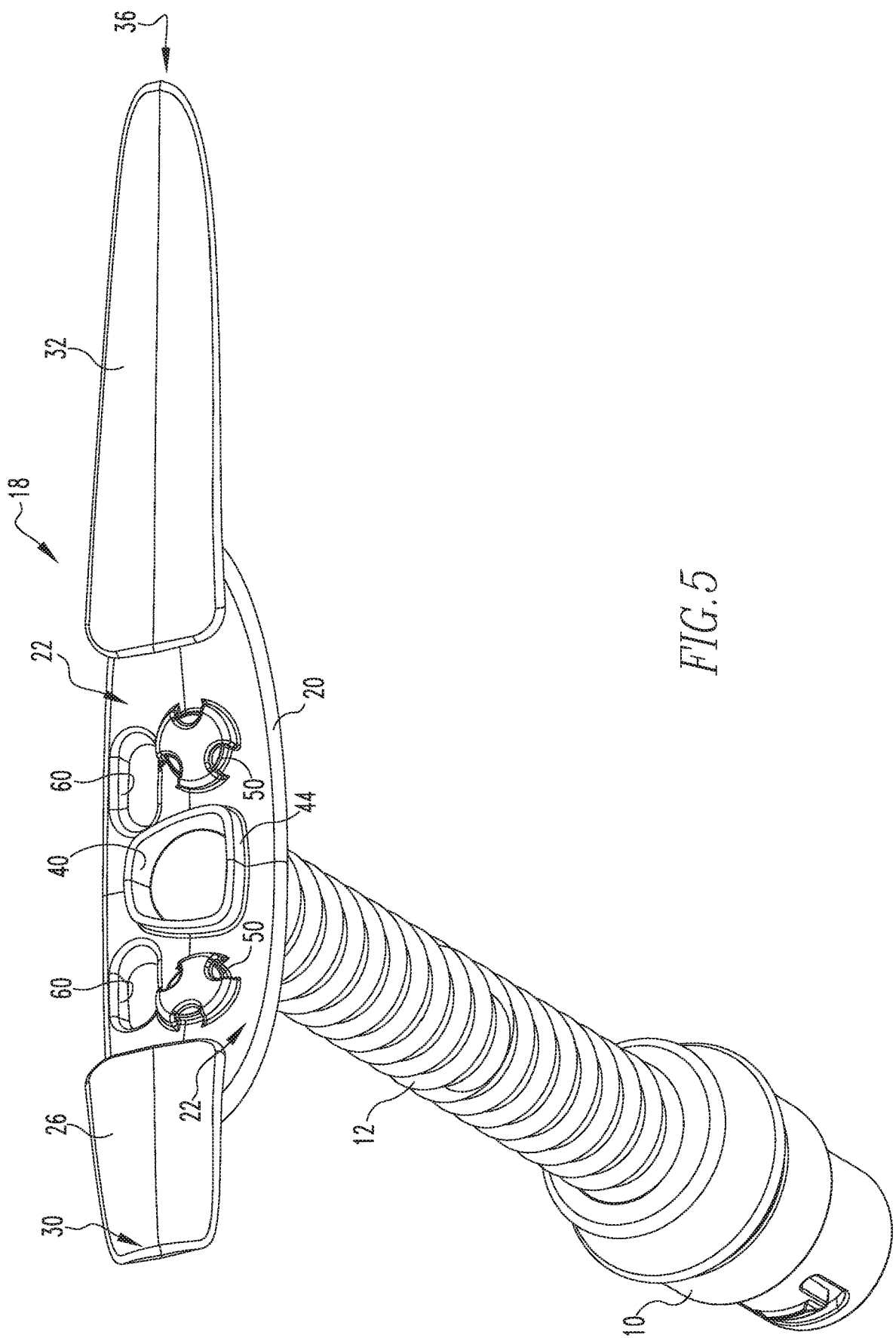
FIG. 5 is a rear isometric view of the frame of the patient interface device of FIG. 1.

Continuing to refer to FIGS. 1 and 2, as well as FIGS. 3-5, frame 18 includes a central portion 20 formed as a generally thin member having a patient facing side 22 and an opposite outward facing side 24. As perhaps best appreciated from the sectional view of FIG. 3, in the example embodiment illustrated, central portion 20 is curved such that patient facing side 22 is generally concave-shaped, while outward facing side 24 is generally convexly-shaped. Frame 18 further includes a first wing portion 26, which extends generally from a first end 28 of central portion 20 in a slightly tapering manner to a first distal tip 30; and a second wing portion 32, which extends generally from a second end 34 of central portion 20 in a slightly tapering manner to a second distal tip 36. As shown in FIG. 3, in the example illustrated embodiment, each of first and second wing portions 26 and 32 are each offset a distance d from patient facing side 22 of central portion 20 by a respective spacer portion (shown generally at 36 and 38) which are each of narrower dimensions than the portions of central portion 20 and wing portions 26 and 32 immediately adjacent thereto.

Referring to the exploded and assembled views of FIGS. 4 and 1, each wing portion 26 and 32 is structured to cooperatively engage a respective one of headgear straps 14 in a manner that secures each strap 14 to frame 18. More particularly, each strap 14 is formed from an elastic fabric material as a generally flattened tubular member having a closed leading end 14A. An aperture 14B which provides access to the inner portion of each flattened tubular member is defined in each strap 14 a distance dl from closed leading end 14A thereof. To secure a strap 14 to frame 18, distal portion 30 of wing portion 26 is inserted into aperture 14B of a strap 14. Aperture 14B is then slid along wing portion 26 until an outward facing portion of the perimeter of aperture 14B contacts spacer portion 36. At such time, the majority of wing portion 26 is positioned inside the flattened tubular member which is strap 14. Next, aperture 14B is generally stretched around the remaining portion of wing portion 26 such that the previously remaining portion of wing portion 26 is positioning in the portion of the flattened tubular member generally between aperture 14B and sealed end 14A and aperture 14B is disposed encircling spacer portion 36, thus securing strap 14 to frame 18. The other strap 14 is likewise secured to frame 18 by repeating the same steps with second wing portion 32. It is to be appreciated that straps 14 may be used with any suitable headgear without varying from the scope of the present invention.

Referring now to FIGS. 3, 5, 8 and 9, central portion 20 includes an aperture 40 defined therethrough for communicating a flow of breathing gas received from conduit 6 through central portion 20 from outward facing side 24 to patient facing side 22. In the example illustrated embodiment, aperture 40 includes a generally threaded portion 42 (FIG. 3) having a diameter D (generally defined by the inner diameter of conduit segment 12). Threaded portion 42 extends from outward facing side 24 toward patient facing side and is sized and configured to cooperatively engage an end portion of conduit segment 12, such that conduit segment may be readily securely coupled thereto (e.g., via an adhesive or other suitable arrangement). It is to be appreciated, however, that aperture 40 may instead be structured to be coupled directly or via a suitable coupling conduit (e.g., an elbow or straight connector) without varying from the scope of the present invention.

On patient facing side 22, aperture 40 is defined by a wall 44 which extends outward from patient facing side 22 forming a hub. Preferably, aperture 40 is made as large as possible in order to diffuse the airflow exiting conduit segment 12 as much as possible. In the example embodiment illustrated, wall 44 forms a slightly trapezoidal-shaped hub when viewed looking along a centerline 46 of aperture 40. Such trapezoidal-shape was generally utilized in such embodiment as such shape maximized the area of aperture within the useable area among other elements contained in central portion 20. In such arrangement, it is thus to be appreciated that aperture 40 transitions from a circular cross section at outward facing side 24 to a generally trapezoidal cross section at patient facing side 22. In addition to maximizing the area of aperture for the given application, the trapezoidal shape also makes it very difficult for a patient to close the hole with the tip of their nose.

For securing frame 18 to cushion 16, frame 18 further includes a plurality (two are included in the illustrated embodiment) of magnetic elements 50 secured (e.g., via over-molding) on or in patient facing side 22 of central portion 20 on opposing sides of aperture 40. Each magnetic element 50 is positioned in central portion 20 such that an outward facing surface (i.e., facing cushion 16) of each element 50 generally protrudes outward from patient facing side 22 (as shown) or is recessed (not shown) into patient facing side 22 of central portion 20. A more detailed description of the positioning and function of each magnetic element 50 is discussed below. In the example illustrated embodiment, each of magnetic elements 50 comprise an axially magnetized disc magnet 50, however, it is to be appreciated that other suitable magnets and/or magnetic materials may be employed without varying from the scope of the present invention.

Frame 18 may further include a number of smaller apertures 60 (two are shown in the illustrated embodiment) disposed about aperture 40. Further details and the function of each aperture 60 is discussed further below.

Figure 6:
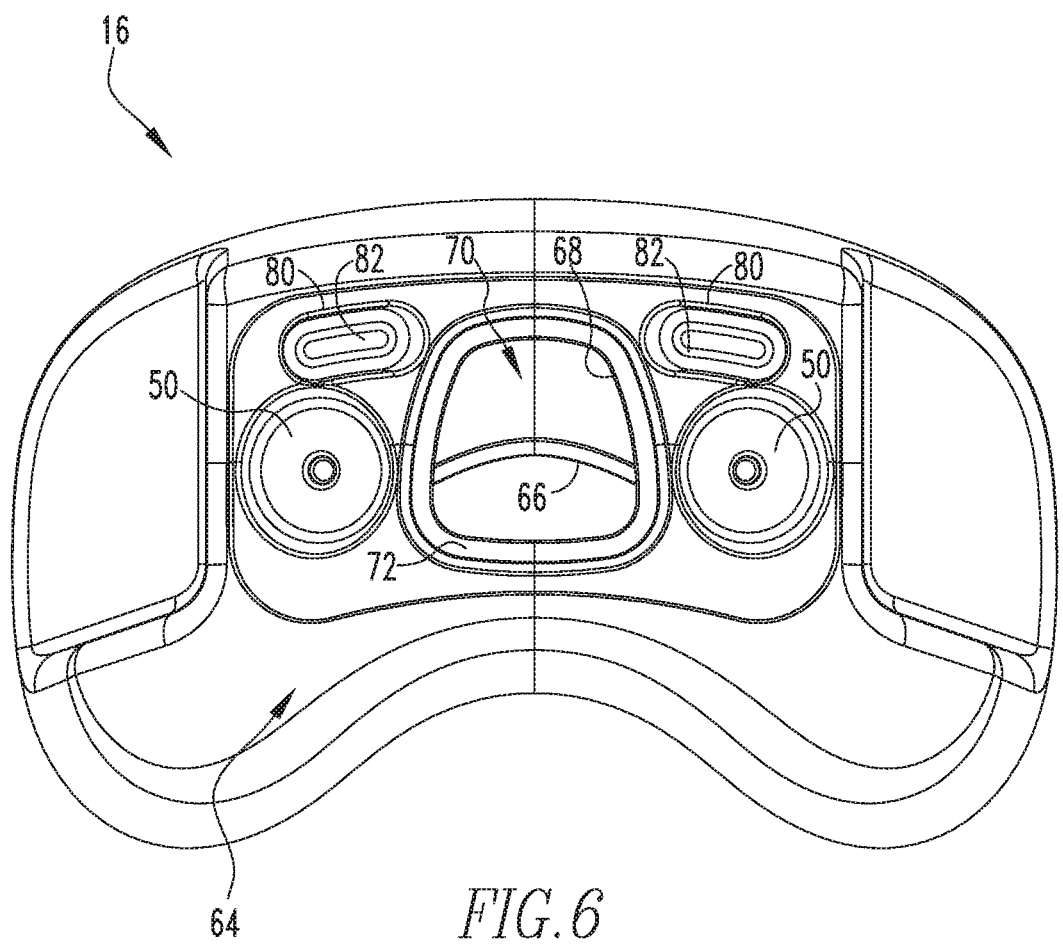
FIG. 6 is a front elevation view of the cushion of the patient interface device of FIG. 1.
Figure 7:
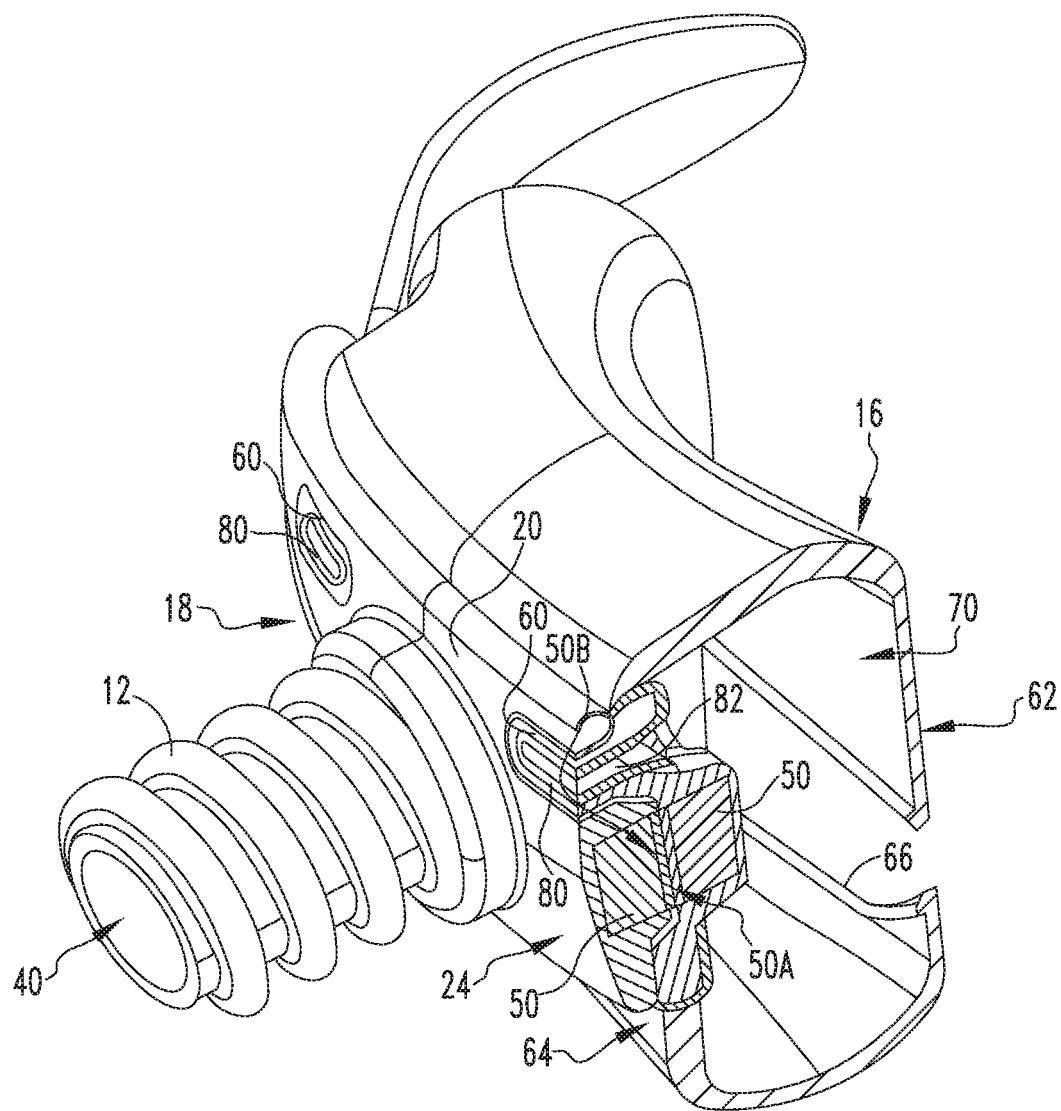
FIG. 7 is a sectional view of the patient interface device of FIG. 1 taken along line 7-7 of FIG. 1.

Referring now generally to FIGS. 2, 4 and 6, cushion 16 includes a patient contacting side 62, preferably formed from a pliable material (e.g., without limitation, silicone), which is structured to sealingly engage about an orifice or orifices of a patient and a frame contacting side 64, preferably formed from a stiffer material (e.g., without limitation, a stiffer silicone, plastic), disposed opposite patient contacting side 62. In the example illustrated, cushion 16 is a nasal cradle, and thus patient contacting side 62 includes a single opening 66 (FIG. 2) which is sized and configured to receive both of the nares of a patient. It is to be appreciated that cushion 16 may instead be of a nasal pillows arrangement or any other suitable patient interface arrangement without varying from the scope of the present invention. Frame contacting side 64 includes an aperture 68 defined therein. Aperture 68 is sized and configured to engage about the hub of central portion 20 of frame 18 formed by wall 44 and is structured to provide for the passage of the flow of breathing gas passing through aperture 40 of central portion 20 of frame 18 to enter a cavity 70 defined in cushion 16 generally between patient contacting side 62 and frame contacting side 64 (which then passes through opening 66 to the nares of the patient).

In order to avoid leakage of the flow of breathing gas passing through apertures 40 and 68, aperture 68 is bounded by a sealing lip 72, preferably formed from a flexible material (e.g., silicone) which is correspondingly-shaped so as to sealingly engage with wall 44 which extends from central portion 20 of frame 18 about aperture 40 thereof. As shown in FIG. 3, in the illustrated example, sealing lip 72 is angled back toward cavity 70, so as to readily align and consistently engage with wall 44. The trapezoidal shape of wall 44 and thus sealing lip 72 provides for a greater sealing area between frame 18 and cushion 16 than a circular arrangement.

For securing cushion 16 to frame 18, cushion 16 further includes a plurality (two are included in the illustrated embodiment) of magnetic elements 50 secured (e.g., via over-molding, press-fit, snap-fit, ultrasonic weld) on or in frame facing side 64 of cushion 16 on opposing sides of aperture 68, so as to correspond with magnets 50 of frame 18 previously discussed. Each magnetic element 50 is positioned such that an outward facing surface (i.e., facing frame 18) of each magnetic element 50 generally is recessed into frame facing side 64 (as shown) or protrudes (not shown) from frame facing side 64 so as to cooperatively engage with the corresponding magnetic element 50 of frame 18 in a manner such that cushion 16 is not only magnetically coupled to frame 18, but also is generally prevented from any potential rotation between cushion 16 and frame 18. As shown in the example of FIG. 3, in order to promote alignment of such protrusions 50A and recesses 50B, preferably each of such elements are cooperatively tapered. Although frame 18 is shown with protruding magnet portions which cooperatively engage recessed portions in cushion 16, it is to be appreciated that one or both of such cooperating features may be reversed without varying from the scope of the present invention.

As an additional anti-rotation feature, cushion 16 may further include a number (two are shown in the illustrated embodiment) of protruding elements 80 extending from frame facing side 64 about aperture 68. Each protruding element 80 is positioned to be cooperatively received in a corresponding one of smaller aperture 60 defined in central portion 20 of frame 18. Similar to the arrangement of protrusions and recesses previously discussed, each protruding element 80 is preferably tapered so as to promote alignment with a corresponding smaller aperture 60 and provide a tight fit therein once fully engaged. In the illustrated example, each protruding element 80 defines an exhalation port 82 therethrough which is structured to allow the passage of gases from cavity 70 to pass therethrough.

Figure 8:
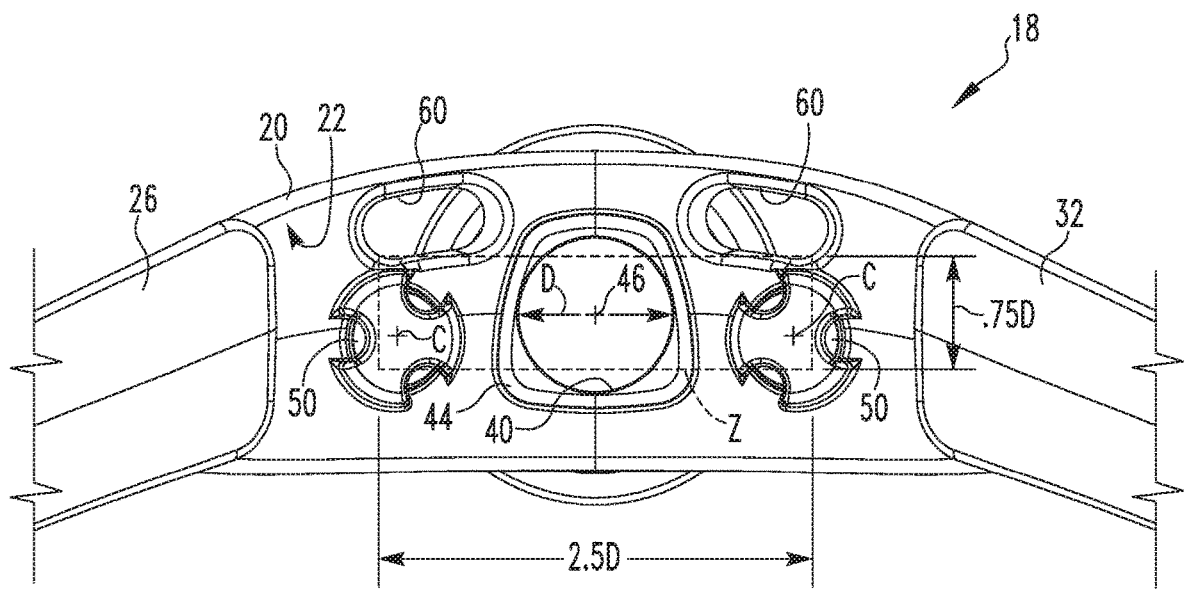
FIG. 8 is a rear elevation view of the frame of the patient interface device of FIG. 1.
Figure 9:
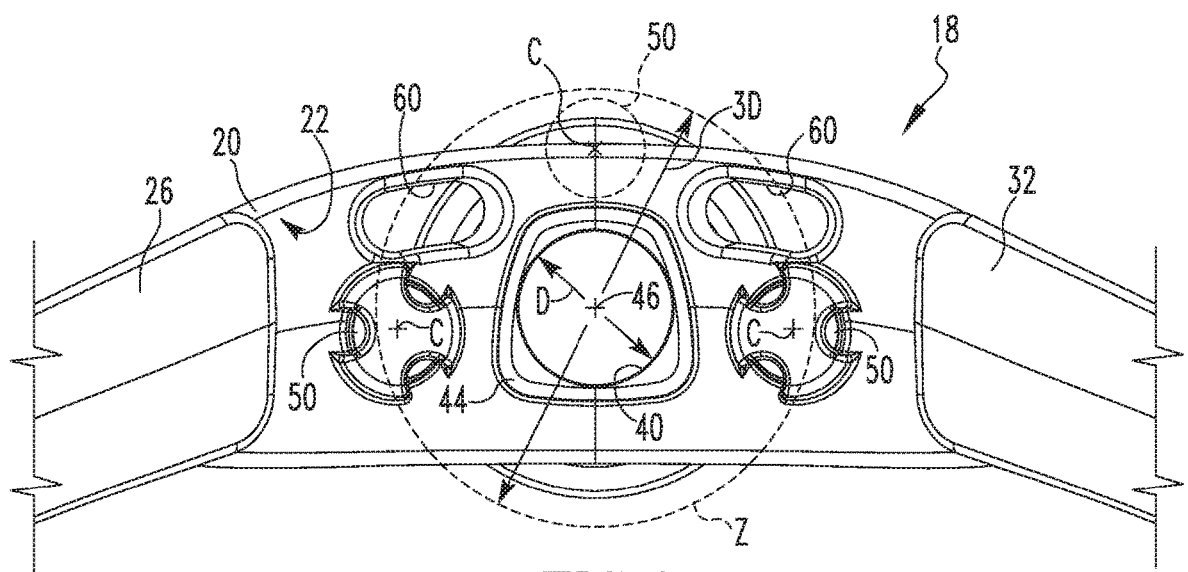
FIG. 9 is a rear elevation view of an alternate version of the frame of FIG. 1 in accordance with another example embodiment of the present invention.

Placement of magnetic elements 50 is extremely important for providing a smooth, reliable magnetic cushion attaching mechanism. FIGS. 8 and 9 illustrate guidelines for optimal magnet placement. More particularly, FIG. 8 illustrates an optimal placement zone Z in which the centers C of axial magnets 50 should generally be located. Zone Z is centered about centerline 46 of aperture 40 and has a height of 0.75×diameter D of aperture 40 and a width of 2.5× diameter D of aperture 40. FIG. 9 similarly illustrates an optimal placement zone Z if more than 2 magnets are employed. In such example, zone Z is defined by a circle centered on centerline 46 of aperture 40 and having a diameter three times diameter D (i.e., 3×D) of aperture 40. Placement outside of these zones can lead to occasional misalignment, kick-standing, and the need for more accurate placement by the user. For example, magnets placed too far apart can misalign and stick before the second pair of magnets are within range of each other. When one magnetic field between a pair of magnets is pulling, the other magnetic field may be out of range. A misaligned cushion will kick-stand on the hub (i.e., wall 44).

Figure 10:
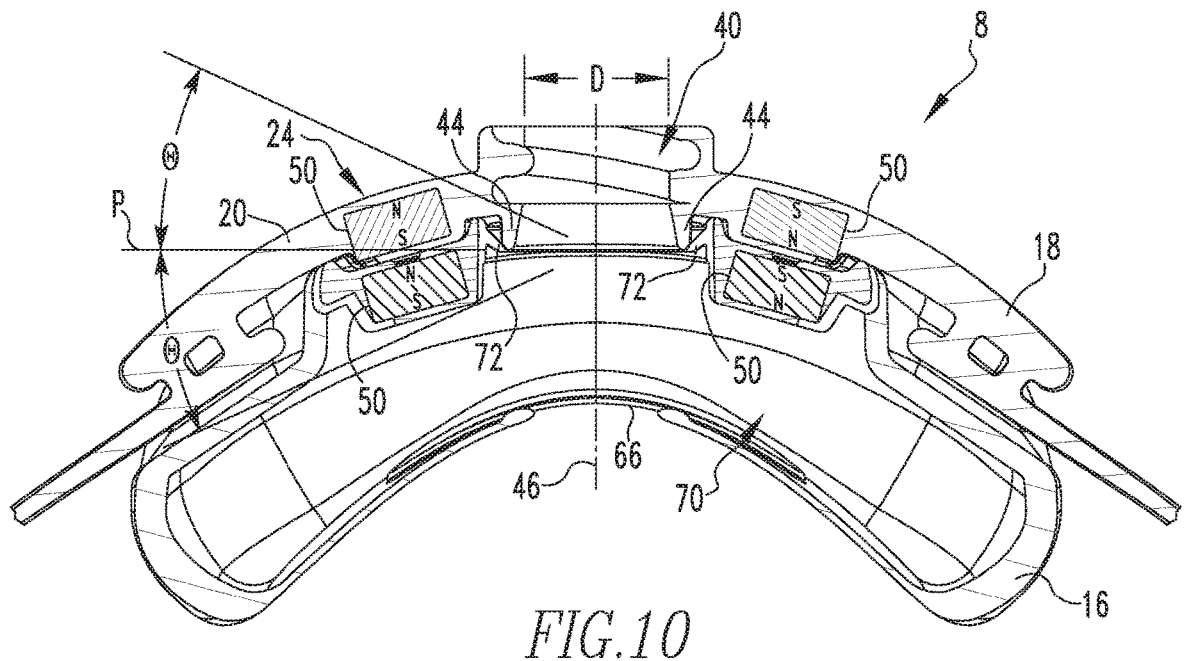
FIG. 10 is a sectional view of a cushion and magnets of a corresponding frame according to one example embodiment of the present invention.

Magnets placed more closely to the hub will not misalign or kick-stand. By the time one magnetic field is pulling and aligning, the other field is within range and begins aligning/pulling. As shown in FIG. 10, ideally, magnets 50 should be placed such that the adjacent faces thereof are in the same plane P as the hub (i.e., wall 44), however, such placement is not always practical for a given application. In such applications where such placement is not practical, the maximum angle θ that the adjacent faces of magnets 50 make from plane P is 25°. Magnets leaned too far inwards (i.e., more than) 25° will tend to fight each other and the cushion 16 will need to be much closer to frame 18 before the magnets pull cushion 16 to frame 18.

Figure 11:
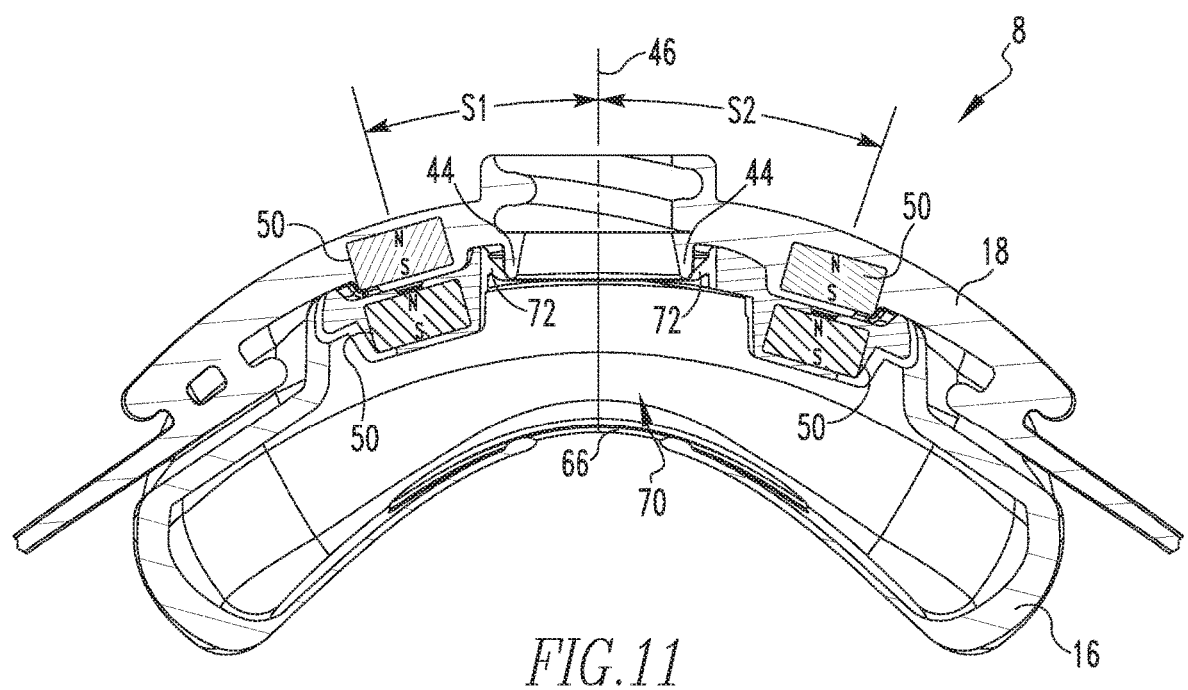
FIG. 11 is a sectional view of a cushion and magnets of a corresponding frame according to another example embodiment of the present invention.

Continuing to refer to FIG. 10, in order to avoid cushion 16 from becoming magnetically coupled, or partially magnetically coupled to frame 18 upside down (i.e., 180° about centerline 46 from proper alignment), magnets 50 may be arranged such that one magnet 50 of frame 18 is oriented with the poles thereof in a first orientation (e.g., with the north end facing toward outward facing side 24 of central portion 20) and the other magnet 50 of frame 18 oriented with the poles thereof in a second orientation, opposite the first orientation (e.g., with the north end facing away from outward facing side 24 of central portion 20). With the corresponding magnets 50 of cushion 16 similarly arranged, a 180° mis-alignment is impossible as the mis-paired magnets 50 would simply repel each other, thus avoiding an unwanted coupling and providing an indication of the attempted misalignment. An example of another solution to avoid such 180° mis-alignment is illustrated in FIG. 11. In such example, magnets 50 of one magnetic pair are spaced generally a first distance S1 from centerline 46, while magnets 50 of the other magnetic pair are spaced a second distance S2, different from the first distance.

As yet another example solution, in place of using two pair of four magnets 50, two pairs, each consisting of one magnet 50 and one steel member may be used. In such example, frame 18 includes one magnet 50 and one steel member, while cushion 16 likewise includes one of each, arranged such that when correctly aligned, the magnet 50 of frame 18 is magnetically coupled to the steel member of cushion 16, and likewise, the magnet 50 of cushion 16 is magnetically coupled to the steel member of frame 18. If such arrangement were spun 180° out of alignment, the magnets would repel each other and the steel members would not have any attraction.

From the foregoing examples, it is thus to be appreciated that embodiments of the present invention provide patient interface devices which utilize magnetic coupling features which provide for consistent, dependable connections between cushions and frames of patient interface devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for use in delivering a flow of breathing gas to the airway of a patient, the patient interface device comprising:
    a frame having a central portion, the central portion comprising:
        a patient facing side;
        an opposite outward facing side;
        a first aperture defined therethrough, the first aperture having a first portion extending from the outward facing side toward the patient facing side which is structured to be coupled to a delivery conduit providing the flow of breathing gas, and a patient side portion defined by a wall which extends outward from the patient facing side forming a hub; and
        a first plurality of magnetic elements, each magnetic element of the first plurality of magnetic elements being secured on or in the patient facing side; and
    a cushion comprising:
        a patient contacting side which is structured to sealingly engage about an orifice or orifices of a patient;
        a frame contacting side disposed opposite the patient contacting side, the frame contacting side including a second aperture defined therein which is sized and configured to engage about the hub of the central portion of the frame and is structured to provide for passage of the flow of breathing gas passing through the first aperture of the central portion of the frame to enter a cavity defined in the cushion generally between the patient contacting side and the frame contacting side; and
        a second plurality of magnetic elements, each magnetic element of the second plurality of magnetic elements being secured on or in the frame contacting side of the cushion in a corresponding position to each magnetic element of the first plurality of magnetic elements of the frame such that the cushion is magnetically coupled to the frame.

2. The patient interface device of claim 1, wherein the first plurality of magnetic elements comprise a first magnetic element disposed on a first side of the first aperture and a second magnetic element disposed on a second side of the first aperture.

3. The patient interface device of claim 2, wherein the first magnetic element comprises a first axial magnet with magnetic poles disposed in a first orientation; and wherein the second magnetic element comprises a second axial magnet with magnetic poles disposed in a second orientation opposite the first orientation.

4. The patient interface device of claim 2, wherein the first magnetic element is disposed a first distance from a centerline of the first aperture and wherein the second magnetic element is disposed a second distance, different than the first distance, from the centerline.

5. The patient interface device of claim 1, wherein each magnetic element of the first plurality of magnetic elements is positioned in the central portion such that a cushion facing surface of each magnetic element generally protrudes outward from the patient facing side of the central portion or is recessed into the patient facing side of the central portion; and
wherein each magnetic element of the second plurality of magnetic elements is positioned such that a frame facing surface of each magnetic element is generally recessed into the frame facing side of the cushion or protrudes outward from the from frame facing side of the cushion so as to cooperatively engage with the corresponding magnetic element of the first plurality of magnetic elements of the frame.

6. The patient interface device of claim 5, wherein each magnetic element of the first plurality of magnetic elements is disposed in one of a protruding portion or a recessed portion of the central portion of the frame; wherein each magnetic element of the second plurality of magnetic elements is disposed in one of a protruding portion or a recessed portion of the cushion; and wherein the protruding portion and recessed portions of the frame and the cushion are cooperatively tapered.

7. The patient interface device of claim 1, wherein the first aperture has a diameter (D); wherein each magnetic element of the first plurality of magnetic elements comprise an axial magnet having a center (C); wherein the center of each magnet is positioned within a zone (Z); and wherein the zone is centered about a centerline of the first aperture and has a height of 75% of the diameter and a width of 250% of the diameter.

8. The patient interface device of claim 1, wherein the first aperture has a diameter (D); wherein each magnetic element of the first plurality of magnetic elements comprise an axial magnet having a center (C); wherein the center of each magnet is positioned within a zone (Z); and wherein the zone is centered about a centerline 46 of the first aperture and has a diameter 250% of the diameter of the first aperture.

9. The patient interface device of claim 1, wherein the first aperture has a diameter (D); wherein each magnetic element of the first plurality of magnetic elements comprise an axial magnet having a center (C); wherein the center of each magnet is positioned within a zone (Z); and wherein the zone is centered about a centerline 46 of the first aperture and has a diameter 300% of the diameter of the first aperture.

10. The patient interface device of claim 1, wherein the hub lies in a plane (P); wherein each magnetic element of the first plurality of magnetic elements is positioned in the central portion such that a cushion facing surface of each magnetic element forms an angle ($\theta$) with respect to the plane which is at most 25°; and wherein each magnetic element of the second plurality of magnetic elements is positioned such that a frame facing surface of each magnetic element forms another angle with respect to the plane which is at most 25°.

11. The patient interface device of claim 1, wherein the hub lies in a plane (P); wherein each magnetic element of the first plurality of magnetic elements is positioned in the central portion such that a cushion facing surface of each magnetic element lies in the plane; and wherein each magnetic element of the second plurality of magnetic elements is positioned such that a frame facing surface of each magnetic element lies in the plane.

12. The patient interface device of claim 1, wherein each magnetic element comprises an axially magnetized disc magnet.

13. The patient interface device of claim 1, wherein the second aperture of the cushion is bounded by a sealing lip which is correspondingly-shaped so as to sealingly engage with the wall which extends from the central portion of the frame about the first aperture.

14. The patient interface device of claim 1, wherein second aperture has a larger cross-sectional area than a cross-sectional area of the first aperture.

15. The patient interface device of claim 1, wherein a first portion of the first aperture comprises a generally threaded portion that is sized and configured to cooperatively engage an end portion of a conduit segment.

16. The patient interface device of claim 1, wherein the central portion is curved such that patient facing side is generally concave-shaped, while outward facing side is generally convexly-shaped.

17. The patient interface device of claim 1, wherein the hub is trapezoidal-shaped when viewed looking along a centerline of the aperture.

18. The patient interface device of claim 1, wherein the frame further includes a first wing portion that extends generally from a first end of the central portion that tapers to a first distal tip, and a second wing portion that extends generally from a second end of the central portion that tapers to a second distal tip.

19. The patient interface device of claim 18, wherein each of the first wing portion and the second wing portion are each offset a distance (d) from the patient facing side of the central portion by a respective spacer portion, which are each of narrower dimensions than the portions of central portion and first and second wing portions immediately adjacent thereto.

20. The patient interface device of claim 1, wherein the frame includes a number of secondary apertures disposed about the first aperture; wherein the cushion includes a corresponding number of protruding elements extending from the frame facing side of the cushion; and wherein each protruding element is cooperatively received in a corresponding one of the secondary apertures.

* * * * *